United States Patent
Lee et al.

(10) Patent No.: US 11,333,608 B2
(45) Date of Patent: May 17, 2022

(54) TARGET GENE-DETECTING DEVICE AND METHOD FOR DETECTING TARGET GENE, USING SAME

(71) Applicant: Samsung Life Public Welfare Foundation, Seoul (KR)

(72) Inventors: Min Young Lee, Seoul (KR); Min Hee Kang, Seoul (KR); Hyun Ju Park, Seoul (KR); Dong Ho Kim, Changwon-si (KR); Sung Gyu Park, Changwon-si (KR); Ho Sang Jung, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 0 days.

(21) Appl. No.: 16/642,130

(22) PCT Filed: Aug. 28, 2018

(86) PCT No.: PCT/KR2018/009899
§ 371 (c)(1),
(2) Date: Feb. 26, 2020

(87) PCT Pub. No.: WO2019/045406
PCT Pub. Date: Mar. 7, 2019

(65) Prior Publication Data
US 2020/0355615 A1    Nov. 12, 2020

(30) Foreign Application Priority Data
Aug. 28, 2017  (KR) .......................... 10-2017-0108848

(51) Int. Cl.
*G01N 33/487* (2006.01)
*G01N 21/65* (2006.01)

(52) U.S. Cl.
CPC ......... *G01N 21/658* (2013.01); *G01N 33/487* (2013.01)

(58) Field of Classification Search
CPC .................. G01N 21/658; G01N 33/48; B01J 2219/00722
See application file for complete search history.

(56) References Cited

U.S. PATENT DOCUMENTS 6,002,471 A    12/1999  Quake
6,127,120 A *  10/2000  Graham ............... C12Q 1/6816
                                                435/6.14
(Continued)

FOREIGN PATENT DOCUMENTS

AU    2007217765 A1 *  8/2007  ........... B01L 3/5023
CN    107419007 A   *  12/2017
(Continued)

OTHER PUBLICATIONS

Li Yao, "In Vitro Isothermal Nucleic Acid Amplification Assisted Surface-Enhanced Raman Spectroscopic for Ultrasensitive Detection of Vibrio parahaemolyticus", ACS Aug. 23, 2017 (Year: 2017).*
(Continued)

*Primary Examiner* — Maurice C Smith
(74) *Attorney, Agent, or Firm* — McCarter & English, LLP

(57) ABSTRACT

The present invention relates to a target gene-detecting device and a method for detecting a target gene. According to an aspect, a target gene-detecting device can be conveniently fabricated at low cost by employing a porous substrate or a method for detecting a target gene allows the pretreatment of a sample, the extraction of a nucleic acid, the amplification of a nucleic acid, and the detection of a target gene to be conducted at high accuracy and specificity in an
(Continued)

integral system, with no contamination plausibility and can be thus useful for gene inspection.

5 Claims, 7 Drawing Sheets

(56) References Cited

U.S. PATENT DOCUMENTS

| | | | |
|---|---|---|---|
| 6,623,977 B1* | 9/2003 | Farquharson | G01N 21/658 |
| | | | 356/301 |
| 6,970,239 B2 | 11/2005 | Chan et al. | |
| 8,481,261 B2 | 7/2013 | Lim et al. | |
| 8,786,852 B2 | 7/2014 | Bond et al. | |
| 2005/0196876 A1 | 9/2005 | Chan et al. | |
| 2006/0215154 A1* | 9/2006 | Chan | G01J 3/44 |
| | | | 356/244 |
| 2008/0176768 A1* | 7/2008 | Zheng | B82Y 30/00 |
| | | | 506/21 |
| 2009/0195783 A1* | 8/2009 | Tazuke | G01N 21/553 |
| | | | 356/445 |
| 2010/0177306 A1* | 7/2010 | Natan | G01N 21/658 |
| | | | 356/301 |
| 2010/0291599 A1* | 11/2010 | Tague, Jr | G01N 21/658 |
| | | | 435/7.92 |
| 2013/0040292 A1* | 2/2013 | Fernandez Lopez | B82Y 15/00 |
| | | | 435/6.11 |
| 2015/0002842 A1 | 1/2015 | Kim et al. | |
| 2015/0275192 A1* | 10/2015 | Holliger | C12N 9/1241 |
| | | | 435/91.5 |
| 2016/0069810 A1 | 3/2016 | Walavalkar et al. | |
| 2017/0030836 A1 | 2/2017 | Kim | |

FOREIGN PATENT DOCUMENTS

| | | | |
|---|---|---|---|
| JP | 2017-517008 A | | 6/2017 |
| KR | 10-2005-0013571 A | | 2/2005 |
| KR | 10-2007-0001936 A | | 1/2007 |
| KR | 10-2010-0001827 A | | 1/2010 |
| KR | 20170140901 A | * | 12/2017 |

OTHER PUBLICATIONS

Jeon, Tae Yoon et al.: "Nanostructured plasmonic substrates for use as SERS sensors", *Nano Convergence*, 2016, vol. 3, 18, pp. 1-20.
International Search Report and Written Opinion prepared by the Korean Intellectual Property Office, acting as the International Searching Authority, for International Application PCT/KR2018/009899 dated Feb. 11, 2019.

* cited by examiner

1: 10ng/uL    2: 1ng/uL    3: 0.1ng/uL    4: NTC

TARGET GENE-DETECTING DEVICE AND METHOD FOR DETECTING TARGET GENE, USING SAME

TECHNICAL FIELD

This application is the National Stage entry under 35 U.S.C § 371 of International Application Number PCT/KR2018/009899 filed Aug. 28, 2018, published on Mar. 7, 2019 under publication number WO 2019/045406 A2, which claims the benefit of priority under 35 U.S.C. § 119 of Korean Patent Application No. 10-2017-0108848, filed Aug. 28, 2017, the disclosure of which is incorporated herein by reference in its entirety.

BACKGROUND ART

With the recent ecosystem changes and transportation development, the likelihood of a mass outbreak of infectious diseases is on the rise, and diagnostic inspection of such infectious diseases is usually conducted through gene diagnosis. Although genetic diagnostic testing is essentially conducted for the diagnosis of an infectious disease, the genetic diagnostic testing is quite a complicated and time-consuming process because three steps of nucleic acid extraction, amplification, and detection need to be performed and high-priced, large-sized equipment is required, making it difficult to quickly diagnose and treat a disease on the spot. Therefore, there is a need for development of a system capable of quickly diagnosing an infectious disease in one device.

Although research into porous membrane-based genetic diagnostic testing methods is currently ongoing, the porous membrane-based genetic diagnostic testing methods may pose several disadvantages, including markedly low sensitivity, compared to solution-based gene amplification, and time-consuming amplification.

Therefore, in order to quickly and accurately detect the presence of a target gene on the spot, there is a need for research into a porous membrane-based gene detection system, which is conveniently fabricated and demonstrates excellent sensitivity.

DESCRIPTION OF EMBODIMENTS

Technical Problem

An aspect of the present invention provides a target gene-detecting device.

Another aspect of the present invention provides a method for detecting a target gene.

Solution to Problem

According to an aspect, there is provided a target gene-detecting device comprising: a first porous substrate supporting a composition for nucleic acid detection; and a second porous substrate having a metal nanostructure.

The first porous substrate may pretreat a biological sample and may extract a nucleic acid. The first porous substrate may support the composition for nucleic acid detection. The composition for nucleic acid detection may include a cell-lysing composition, a composition for protein degradation, a composition for suppressing nucleic acid degradation, or a combination thereof. The cell-lysing composition, the composition for protein degradation, the composition for suppressing nucleic acid degradation, or the combination thereof may completely or substantially eliminate substances which inhibit the acquisition of a nucleic acid, such as a non-nucleic acid substance that is present in the biological sample, a protein, or an impurity. The cell-lysing composition, the composition for protein degradation, the composition for suppressing nucleic acid degradation, or the combination thereof may be selected by a person skilled in the art according to the kind of biological sample used. The cell-lysing composition, the composition for protein degradation, the composition for suppressing nucleic acid degradation, or the combination thereof may include, but is not limited to, any composition that can be used in the course of breaking down or lysing a cell, degrading or digesting a protein, inhibiting a protein activity, denaturing a protein, or inhibiting a nuclease activity, to extract a nucleic acid from a biological sample, may include, for example, a cell lysis buffer, an alkali solution, for example, an aqueous NaOH solution, a proteinase, an ionic surfactant, a non-ionic surfactant, a phosphate buffered saline, a nuclease inhibitor, or a combination thereof, and may specifically include deoxycholate sodium dodecyl sulfate (SDS), dithiolthreitol (DTT), NP-40, a ribonuclease inhibitor, a deoxyribonuclease inhibitor, or a combination thereof. The composition for nucleic acid detection may include, but is not limited to, any composition that can be used to extract a nucleic acid from a biological sample, and may include, for example, isopropanol, ethanol, phenol, chloroform, guanidine isothiocyanate, Trizol®, or a combination thereof.

The substances contained in the composition for nucleic acid detection may be supported on the first porous substrate simultaneously, sequentially or in any arbitrary order that can be selected by a person skilled in the art.

The supporting means that the composition for nucleic acid detection is contained in the first porous substrate. The supporting may be achieved by submerging, depositing, dispensing or spraying the composition for nucleic acid detection into the skeleton of the first porous substrate. The supporting is not limited to any type as long as the skeleton of the first porous substrate can contain the composition for nucleic acid detection.

The composition for nucleic acid detection may react with the biological sample and thus extracts the nucleic acid with high purity and high yield. The extracted nucleic acid can be safely contained in the first porous substrate.

The second porous substrate may emit a signal of the light scattered after irradiating laser into the device. The second porous substrate may comprise a metal nanostructure. The metal nanostructure may enhance a scattering signal of a nucleic acid when the nucleic acid is present around the metal nanostructure. The enhancing may comprise enhancing about $10^3$ to about $10^{14}$ times, or enhancing about $10^5$ to about $10^8$ times. Certain electron vibration that occurs on the surface of the metal nanostructure, called localized surface plasmon resonance (LSPR), may create an intense electromagnetic field within a predetermined range upon certain laser irradiation, and the created electromagnetic field may interact with a molecule, thereby enhancing a scattering signal of the molecule. The electromagnetic field is particularly intensified between adjacent metal nanostructures, and/or between the molecule and the metal nanostructure, where a scattering signal is shown, and this region is referred to as a hot-spot. The plasmon resonance may vary according to the kind, size and shape of the metal nanostructure, the dispersion solvent, the type of laser, or a combination thereof. The metal nanostructure may comprise gold, silver, platinum, aluminum, iron, zinc, bronze, brass, nickel, alloys of these metals, or a combination thereof. The metal nanostructure may be a metal nanoparticle, a metal nanorod, a metal nanoisland, a metal nanocap, a metal nanowire, a metal nanocrescent moon, a metal nanorice, a metal nanoshell, a metal nanostar, a metal nanosphere, or a combination thereof. The metal nanostructure is not limited as long as the metal nanostructure is positioned adjacent to the inside and/or the outside of the second porous substrate, and examples thereof may include a metal nanostructure patterned on the second porous substrate, a metal nanostructure deposited on the second porous substrate, a metal nanostructure coated on the second porous substrate, or a combination thereof. The size of the metal nanostructure may range from about 4 nm to about 400 nm, from about 8 nm to about 200 nm, from about 20 nm to about 80 nm, from about 20 nm to about 60 nm, or from about 20 nm to about 40 nm. When the metal nanostructure is a metal nanowire, the diameter thereof may range from about 4 nm to about 400 nm, from about 8 nm to about 200 nm, from about 20 nm to about 80 nm, from about 20 nm to about 60 nm, or from about 20 nm to about 40 nm. When the metal nanostructure is a metal nanowire, the length thereof may range from about 5 μm to about 50 μm, from about 10 μm to about 40 μm, from about 12 μm to about 35 μm, from about 15 μm to about 32 μm, or from about 17 μm to about 30 μm.

The second porous substrate may support the nucleic acid-amplifying composition. To specifically amplify a target gene that is present in a sample, the nucleic acid-amplifying composition may be selected by a person skilled in the art according to the kind of sample. The nucleic acid-amplifying composition may comprise, for example, a primer, probe or polymerase capable of specifically amplifying a target gene, for example, Taq. polymerase or Bst. polymerase, a buffer solution, purified water, 4 species of deoxynucleoside triphosphates (dNTPs), MgCl, KCl, or a combination thereof. Designing a primer can be easily performed by a person skilled in the art by referencing given sequences of a target nucleic acid to be amplified. For example, the primer may be designed using a commercially available primer-designing program. Examples of the commercially available primer-designing program include a PRIMER 3 program. The nucleic acid-amplifying composition may be a temperature cycling composition or a composition for isothermal amplification. The composition for isothermal amplification may comprise a Bst. polymerase.

For ease of detecting a target gene, the second porous substrate may comprise a composition for nucleic acid detection. The composition for nucleic acid detection may be a label that directly or indirectly binds to a nucleic acid to be detectable. The composition for nucleic acid detection may comprise a fluorescently labeled material. The fluorescently labeled material may be, for example, SYBR Green, Eva green, a dual-labeled probe having a fluorophore coupled to the 5' terminus thereof and a quencher coupled to the 3' terminus thereof to control prevention of the emission of fluorescence, or a combination thereof. In addition, a calibration factor may be additionally added to the fluorescently labeled material, and the calibration factor of the fluorescently labeled material may be, for example, a material that does not interact with a nucleic acid such as ROX or fluorescein. Generally, when a Raman scattering signal is clinically applied, signal quantification is difficult to achieve, and the reproducibility of the signal quantification is difficult to secure. Therefore, the addition of the calibration factor is advantageous in that quantitative assay is enabled on the basis of the Raman scattering signal of the target gene to be compared with a Raman scattering signal of the calibration factor, and that the reproducibility of Raman scattering signal quantification can be improved. The first porous substrate or the second porous substrate may be in the form of a net, a filter, a membrane, or a combination thereof. The first porous substrate or the second porous substrate may be a porous substrate having fibers interconnected to form pores, a porous substrate having a plurality of perforations formed on the skeleton of a membrane, or a combination thereof. The material of the first porous substrate or the second porous substrate may be paper, nylon, nitrocellulose (NC), polyester (PE), polysulfonate (PS), polyether sulfone (PES), polytetrafluoroethylene (PTFE), polyvinylidene fluoride (PVDF), polypropylene (PP), cellulose, cellulose acetate (CA), regenerated cellulose (RC), glass, or a combination thereof. The first porous substrate and the second porous substrate may have the same material or different materials. The first porous substrate and the second porous substrate may have a porosity ranging from about 10% to about 50%. The first porous substrate is not limited as long as it is capable of supporting the composition for nucleic acid detection, and the second porous substrate is not limited as long as it can be a skeleton having a nanostructure and is capable of maintaining the nanostructure.

The first porous substrate and the second porous substrate may be present in a closed vessel. When the first porous substrate and the second porous substrate are present in the closed vessel, the biological sample and/or the nucleic acid can be prevented from being contaminated by externally transferred impurities, and the nucleic acid extracted by applying pressure to the closed vessel can move from the first porous substrate to the second porous substrate.

The first porous substrate and the second porous substrate may be arranged to be in contact with each other or to be spaced a predetermined distance apart from each other. When the first porous substrate and the second porous substrate are arranged to be in contact with each other, the first porous substrate may be positioned above and the second porous substrate may be positioned below. When the first porous substrate and the second porous substrate are arranged to be in contact with each other, the extracted nucleic acid may move from the first porous substrate to the second porous substrate in direct contact with each other. When the first porous substrate and the second porous substrate are arranged to be spaced a predetermined distance apart from each other, the device may comprise a connection unit 15 that connects the first porous substrate and the second porous substrate to each other. The connection unit 15 may allow the extracted nucleic acid to move from the first porous substrate to the second porous substrate through the same. The connection unit 15 may totally or partially connect the first porous substrate and the second porous substrate to each other. The connection unit 15 may produce an open space or a closed space. When the connection unit 15 produces a closed space, the nucleic acid can be prevented from being contaminated by externally transferred impurities, and the extracted nucleic acid can move from the first porous substrate to the second porous substrate through the connection unit 15 by applying pressure to the closed space. When the connection unit 15 produces an open space, the extracted nucleic acid may naturally fall on the second porous substrate, or extracted nucleic acid can move from the first porous substrate to the second porous substrate by dispensing the extracted nucleic acid to the second porous substrate.

For ease of moving the extracted nucleic acid to the second porous substrate when the biological sample reacts with the composition for nucleic acid detection, the device may comprise a pressure regulator provided in one direction or opposite directions of the first porous substrate and/or the second porous substrate. The pressure regulator may apply an absorption force and/or a discharging force to the first porous substrate and/or the second porous substrate, and thus may regulate the speed of the biological sample contacting the first porous substrate and/or the speed of the extracted nucleic acid moving to the second porous substrate.

The device may emit a scattered light signal after being irradiated with laser. The device may be operably connected to one or more laser sources and a spectrometer. One of non-limiting examples of the spectrometer is disclosed in U.S. Pat. No. 6,002,471. The laser may be emitted from a laser source, and may comprise a pulsed laser beam, a continuous laser beam, or a combination thereof. Beams of the laser may pass a confocal optical device and a microscope lens, and thus focuses thereof may be collected on one or more second porous substrates. The light emitted from the nucleic acid and the nanostructure to which the nucleic acid is brought into proximity may be collected by the microscope lens and the confocal optical device. The light emitted from the nucleic acid and the nanostructure to which the nucleic acid is brought into proximity may be introduced to the spectrometer. The light emitted from the nucleic acid and the nanostructure to which the nucleic acid is brought into proximity may be coupled to the spectrometer to be separated and detected at various wavelengths. The spectrometer may be connected to a computer that counts and digitizes scattering signals via an interface. The scattering signals may be counted and digitized from the spectrum detected, and thus the presence and/or the quantity of a target gene may be detected.

The device comprises: a first porous substrate supporting a composition for nucleic acid detection; and a second porous substrate having a metal nanostructure, wherein, since the nucleic acid extracted from the first porous substrate is contacted with the second porous substrate provided in the device without separately moving the extracted nucleic acid from the first porous substrate to the second porous substrate, a target gene can be detected just by injecting the biological sample into the first porous substrate and irradiating the second porous substrate with laser, thereby conveniently detecting a target nucleic acid and diagnosing a pathogen in real time under any environments without using a special device.

According to another aspect, there is provided a method for detecting a target gene comprising: contacting a biological sample with a first porous substrate supporting a composition for nucleic acid detection and thus extracting a nucleic acid from the biological sample; contacting the extracted nucleic acid with a second porous substrate having a metal nanostructure and thus bringing the nucleic acid into proximity to the metal nanostructure; and acquiring a signal of the light scattered after irradiating with laser the second porous substrate having the nanostructure to which the nucleic acid is brought into proximity.

The method comprises extracting a nucleic acid from the sample by contacting the biological sample with the first porous substrate supporting the composition for nucleic acid detection. The biological sample is not specifically as long as it contains genes, and can be selected by a person skilled in the art according to purposes. The biological sample may include, for example, tissue, a cell, blood, blood plasma, blood serum, saliva, sputum, spinal fluid, urine, or a combination thereof. The contacting is not particularly limited as long as it can cause the biological sample to react with the composition for nucleic acid detection, and may be, for example, dispensing the biological sample to the first porous substrate, depositing the first porous substrate in the biological sample, or a combination thereof.

The nucleic acid is not limited as long as it contains a gene, and may be a deoxyribonucleic acid (DNA), a ribonucleic acid (RNA), a peptide nucleic acid (PNA), a locked nucleic acid (LNA), or a combination thereof. The DNA may be a cDNA, a genomic DNA, or a combination thereof, and the RNA may be an mRNA, a genomic RNA, or a combination thereof. When a target gene is contained in the nucleic acid, a primer or a probe may be hybridized with the target gene.

According to the extracting of the nucleic acid from the sample in the method, the biological sample and the composition for nucleic acid detection may react with each other, thereby extracting the nucleic acid with high purity and high yield. The nucleic acid extracted in the step above is safely contained in the first porous substrate.

The method comprises contacting the extracted nucleic acid with the second porous substrate having a metal nanostructure and thus bringing the nucleic acid into proximity to the metal nanostructure. The contacting is not limited as long as the extracted nucleic acid can be brought into proximity to the metal nanostructure by the contacting, and may comprise, for example, dispensing the extracted nucleic acid to the second porous substrate, depositing the second porous substrate in the extracted nucleic acid, or a combination thereof. The proximity may mean that the nucleic acid is positioned adjacent to the metal nanostructure or is attached to the metal nanostructure. The nucleic acid being positioned adjacent to the metal nanostructure may comprise the nucleic acid being positioned within the distance of several nanometers, for example, d=about 50 nm, d=about 20 nm, d=about 10 nm, d=about 5 nm, d=about 2 nm, or d=about 1 nm.

The method may comprise producing a metal nanostructure. A person skilled in the art may select a method of producing the metal nanostructure according to the kind, size, type, dispersion solvent and laser type of the metal nanostructure, or a combination thereof. The method of producing the metal nanostructure may be, for example, a method of reducing metal nitrates.

The method may comprise producing a second porous substrate having a metal nanostructure. The metal nanostructure may be formed by performing a nano imprinting process, a photolithography process, an electron beam lithography process, a wet etching process, a self-aligned nanostructure producing process, an aluminum cathode oxidation process, a vacuum filtering process, or a combination thereof.

The contacting of the extracted nucleic acid with the second porous substrate having a metal nanostructure may be achieved by moving the extracted nucleic acid from the first porous substrate to the second porous substrate. When the first porous substrate and the second porous substrate are arranged to be spaced apart from each other, the extracted nucleic acid may move from the first porous substrate to the second porous substrate through a connection unit connecting the first porous substrate and the second porous substrate to each other. When the first porous substrate and the second porous substrate are arranged to be in contact with each other, the extracted nucleic acid may move from the first porous substrate to the second porous substrate in direct contact with each other.

The bringing of the nucleic acid into proximity to the metal nanostructure may comprise amplifying the nucleic acid. The amplifying may be performed using the nucleic acid-amplifying composition required for an amplification reaction. The amplifying may be performed by a temperature cycling reaction, an isothermal amplification reaction or a polymerase chain reaction (PCR). The isothermal amplification reaction may amplify a target nucleic acid by performing annealing and extension at a constant temperature. The isothermal amplification reaction may comprise helicase-dependent amplification (HDA), recombinase polymerase amplification (RPA), rolling circle amplification (RCA), loop mediated isothermal amplification (LAMP), nucleic acid-sequence-based amplification (NASBA), transcription mediated amplification (TMA), signal mediated amplification of RNA technology (SMART), strand displacement amplification (SDA), isothermal multiple displacement amplification (IMDA), single primer isothermal amplification (SPIA), circular helicase-dependent amplification (cHDA), or a combination thereof. The isothermal amplification reaction may be carried out at room temperature or at a high temperature ranging from, for example, about 37° C. to about 80° C., or about 50° C. to about 70° C. The isothermal amplification reaction may be carried out using a composition for isothermal amplification, which is required for the isothermal amplification reaction. The polymerase chain reaction may be carried out using an end-point PCR, a real-time PCR, a digital PCR, a multiplex real-time PCR, and other methods that are publicly known in the art.

The method comprises acquiring a signal of the light scattered after irradiating with laser the second porous substrate having a nanostructure to which the nucleic acid is brought into proximity. After irradiating the second porous substrate with the laser emitted from a laser source, the second porous substrate, which includes the nucleic acid and the nanostructure to which the nucleic acid is brought into proximity, emits scattered light. The emitted light is introduced to a spectrometer to then be separated and detected at various wavelengths. A scattering signal may be counted and digitized from the spectrum detected, and thus the presence and/or the quantity of a target gene may be detected. The scattering signal may be a signal of the light scattered from a nucleic acid, a primer or probe used for the detection of a nucleic acid, a detectable label, an amplified nucleic acid, an amplified primer or probe used for the detection of a nucleic acid, or an amplified detectable label. The acquiring of the scattering signal may comprise performing spectrometry.

The scattering may be surface-enhanced Raman scattering (SERS), surface-enhanced resonance Raman scattering (SERRS), coherent anti-stokes Raman scattering (CARS), or a combination thereof. The scattering signal may be a scattering signal intensity, a scattering signal pattern, or a combination thereof. In a specific embodiment, in the case where a nucleic acid is detected by surface-enhanced Raman scattering, scattered light may be enhanced even when the substrate includes a small amount of the nucleic acid, and may then be stably emitted, thereby stably and efficiently acquiring the scattering signal.

In the method, the respective steps may be performed inside or outside a closed vessel.

The first porous substrate supporting the composition for nucleic acid detection, the second porous substrate having a metal nanostructure, the nucleic acid, the movement of the nucleic acid, the amplification, the laser, and the spectrometer are the same as described above.

FIGS. 1A and 1B are schematic diagrams illustrating a target gene-detecting device according to an embodiment.

Referring to FIGS. 1A and 1B, a target gene-detecting device 1 may comprise a first porous substrate 10 supporting a composition for nucleic acid detection; and a second porous substrate 20 connected to the first porous substrate and having a metal nanostructure. The second porous substrate 20 having a metal nanostructure may include a silver nanostructure at one side of the skeleton thereof, as shown in FIG. 2. The second porous substrate 20 may support a nucleic acid-amplifying composition. A sample 30 may be contacted with the first porous substrate 10, thereby extracting a nucleic acid from the sample 30. The extracted nucleic acid may move to the second porous substrate 20 connected to the first porous substrate 10. The extracted nucleic acid may be amplified in the second porous substrate 20, and a target gene may be detected by identifying a scattering signal after irradiating the second porous substrate 20 with laser 60.

Referring to FIG. 1A, a biological sample may be contacted with the first porous substrate 10 to produce a cell-lysed or protein-degraded product 40. The product 40, which contains the nucleic acid extracted from the sample 30, is safely contained in the first porous substrate 10. A composition 50 for nucleic acid detection may be additionally added to the first porous substrate 10, as needed. Referring to FIG. 1B, the first porous substrate 10 and the second porous substrate 20 may be present in a closed vessel.

The method may be for infectious disease diagnosis, genetic disease diagnosis, a pharmacogenetic test, or a combination thereof. The method may be for diagnosing an infectious disease by detecting a foreign gene as a target. The infectious disease may comprise, for example, cytomegalo virus (CMV), hepatitis C virus (HCV), human immunodeficiency Virus (HIV), or hepatitis B virus (HBV). The infectious disease may be *Chlamydia trachomatis, Neisseria gonorrhoeae, Chlamydia trachomatis, Neisseria gonorrhoeae, Gardnerella, Trichomonas vaginalis, Candida* spp, *Streptococci, Staphylococcus aureus, Mycobacterium tuberculosis,* or other infectious diseases on the basis of combinations thereof. The method may be for diagnosing a genetic disease by identifying a genotype or mutation which induces or may potentially induce a particular human disease or symptom. The diagnosis may be used in germ carrier inspection, prenatal testing, or a neonatal screening test. The method may be for a pharmacogenetic test that predicts drug metabolism and responses depending on genetic differences. The pharmacogenetic test may be conducted for screening patients who show responses to drug treatment and patients who show no responses or abnormal responses to drug treatment. As per the pharmacogenetic test, personalized medicine for prescribing drugs for a patient and determining dosages can be achieved.

Advantageous Effects of Disclosure

According to an aspect of the target gene-detecting device or the method for detecting a target gene, the target gene-detecting device can be conveniently fabricated at low cost by employing a porous substrate, and the method can be useful for gene inspection because the pretreatment of a sample, the extraction of a nucleic acid, the amplification of a nucleic acid, and the detection of a target gene are conducted at high accuracy and specificity in an integral system without contamination plausibility.

BEST MODE

Hereinafter, the present invention is described in greater detail by the following examples. However, these examples are provided for illustrating the present invention, not for limiting the scope of the present invention thereto.

EXAMPLE

Production of porous fiber substrate for nucleic acid extraction and porous fiber substrate having silver nanowire for nucleic acid amplification and detection, and detection of nucleic acid using surface-enhanced Raman scattering 1. Production of Porous Fiber Substrate for Nucleic Acid Extraction A porous fiber substrate for the extraction of a nucleic acid from a sample was produced in the following manner. A glass microfiber filter (Whatman, 1827-047) was used as a skeleton of the porous fiber substrate. A solution, which contains a proteinase K, a sputum lysis enzyme (Sputazym, KYOKUTO), sodium dodecyl sulfate (SDS), and dithiothreitol (DTT), was dropped on 1 cm×1 cm glass microfiber filter paper, and then dried at room temperature, thereby producing a first porous substrate supporting a composition for nucleic acid detection.

2. Identification of RNA Acquisition Efficiency from Porous Fiber Substrate for Nucleic Acid Extraction The efficiency of nucleic acid extraction was identified from a biological sample on the substrate produced as in example 1 above. A cell suspension containing sputum and PC12 cell line (Korean Cell Line Bank) was used as the sample. 10 µℓ of a phosphate buffer saline solution having PC12 cells dispersed in a concentration of $10^4$/mℓ was mixed with 250 µℓ of sputum, and the sample including the cell and the sputum mixed therein was then dropped on the produced substrate, followed by reacting at 37° C. for one hour. Following the reaction, the resultant sample was washed with isopropanol several times to thus remove byproducts other than RNAs. Subsequently, the substrate was put into a tube, and 1 mℓ of a phosphate buffer saline solution was added thereto, followed by vortexing. The RNAs that are present in the phosphate buffer saline solution were quantified using a nanodrop. As a control group for the present substrate, the RNAs extracted using an AccuPrep® Viral RNA extraction kit (Bioneer) were used. The result of quantifying the extracted RNAs confirmed that the quantity of the RNAs extracted from the substrate was about 60% that of RNAs extracted using the AccuPrep® Viral RNA extraction kit, suggesting that the RNAs could be extracted with high yield.

3. Production of Porous Fiber Substrate Having Silver Nanowire for Nucleic Acid Amplification and Detection To produce a porous fiber substrate for nucleic acid amplification and acquisition of a surface-enhanced Raman scattering signal, a porous substrate having a silver nanowire combined with glass microfiber filter paper in a 3-dimensional manner using vacuum filtration (Whatman, Model No. 1825-047) was produced.

Figure 1A:
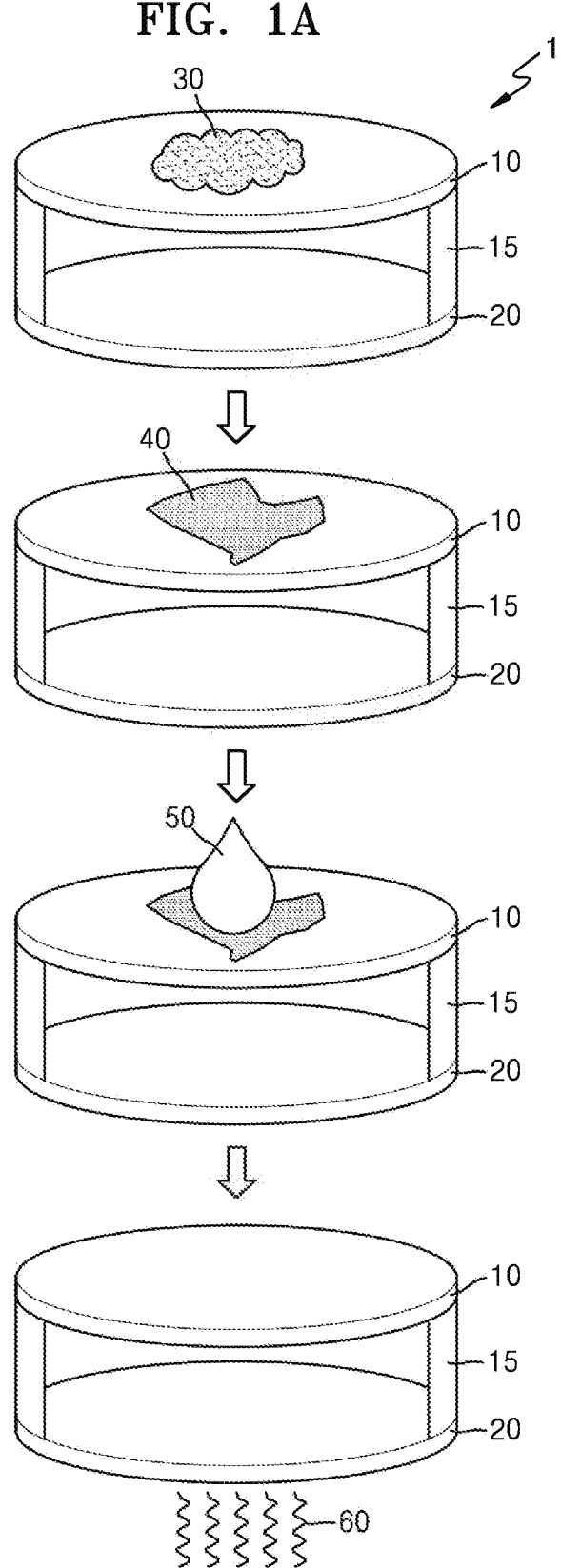
FIG. 1 shows schematic diagrams illustrating a target gene-detecting device according to an embodiment.
Figure 1B:
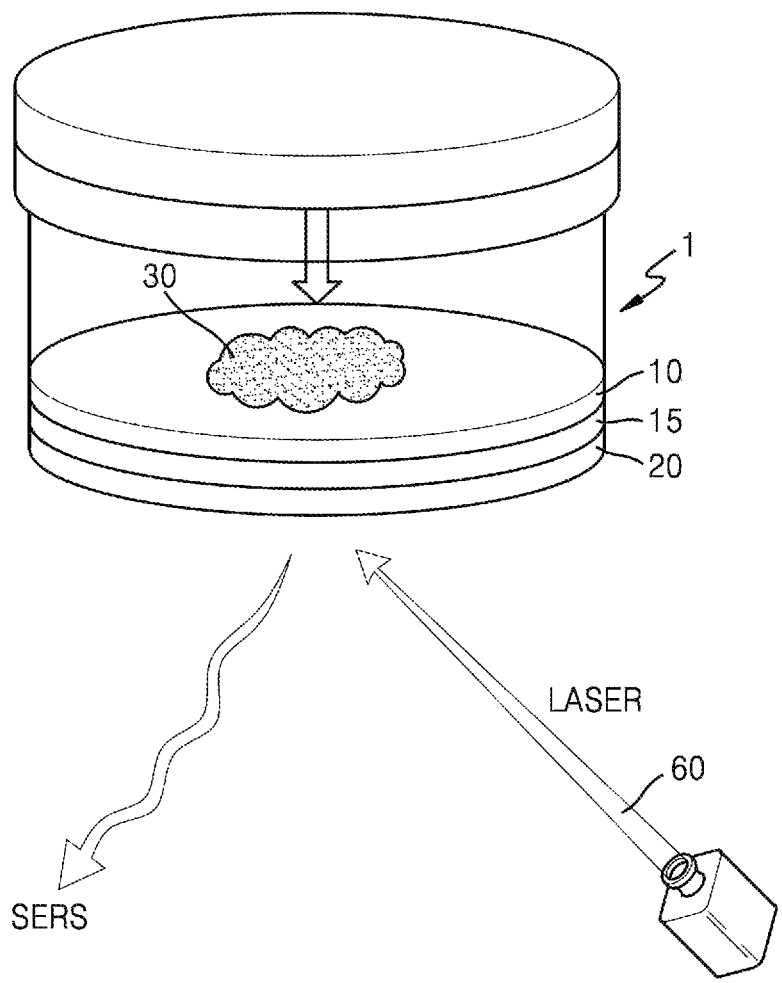
Figure 2:
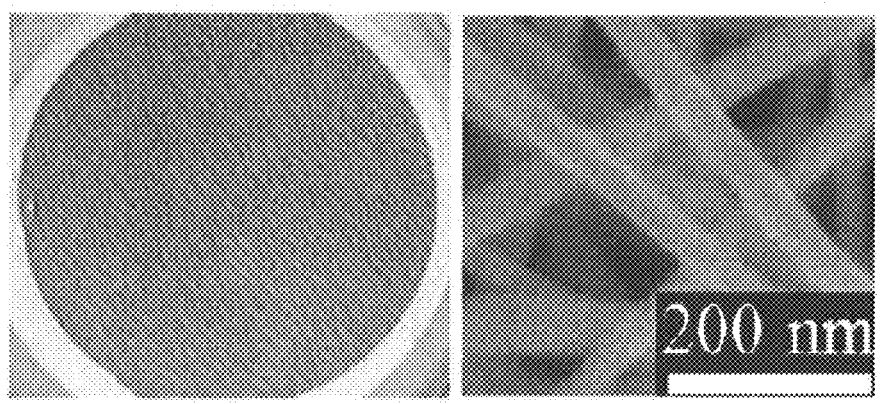
FIG. 2 shows photographs of a second porous substrate having a silver nanowire and a silver nanowire structure included in the second porous substrate, as identified by scanning electron microscope (SEM) imaging.

To a dispersion of a silver nanowire having a diameter of about 30 nm (P/N AgNW-R20W, C3Nano Inc., Korea) was added purified water, preparing a silver nanowire dispersion having about 0.04 wt % of the silver nanowire dispersed in the purified water. 3 mℓ of the prepared silver nanowire dispersion was poured on the glass microfiber filter paper having a diameter of 40 to 50 mm and was then left to be immersed in 5% (v/v) $HNO_3$ solution for 2 minutes for removal of the capping agent contained in the dispersion. After washing with distilled water several times, the washed product was dried on a 170° C. hot plate for 5 minutes, thereby producing a second porous substrate having a metal nanostructure. FIG. 2 shows photographs of a second porous substrate having a silver nanowire and a silver nanowire structure of the second porous substrate, as identified by scanning electron microscope (SEM) imaging. As shown in FIG. 2, it is confirmed that the metal nanostructure is combined with glass microfiber filter paper in a 3-dimensional manner and a hot-spot is formed between nanostructures upon laser irradiation.

4. Detection of Target Gene by Raman-Scattering Isothermal Amplification Product of Nucleic Acid A product obtained by isothermally amplifying a nucleic acid was dropped on the second porous substrate produced as in example 3 above to detect surface-enhanced Raman scattered light, and thus identifying whether the target gene was present in the sample.

Loop-mediated isothermal amplification (LAMP) was selected as an isothermal gene amplification technique, and a LAMP kit (bioassay) fabricated for marine birnavirus was used. A LAMP mix solution including a BST DNA polymerase, a BSP polymerase buffer, a dNTP mix, a LAMP primer mix, SYBR green, and marine birnavirus RNAs, was prepared. Here, the marine birnavirus RNAs were prepared in various concentrations (0, 0.1, 1, and 10 ng/µℓ ). 20 µℓ of the LAMP mix solution was put into a 300 µℓ tube for PCR. After the PCR reaction was conducted at 65° C. for one hour, the reaction was terminated.

Figure 3A:
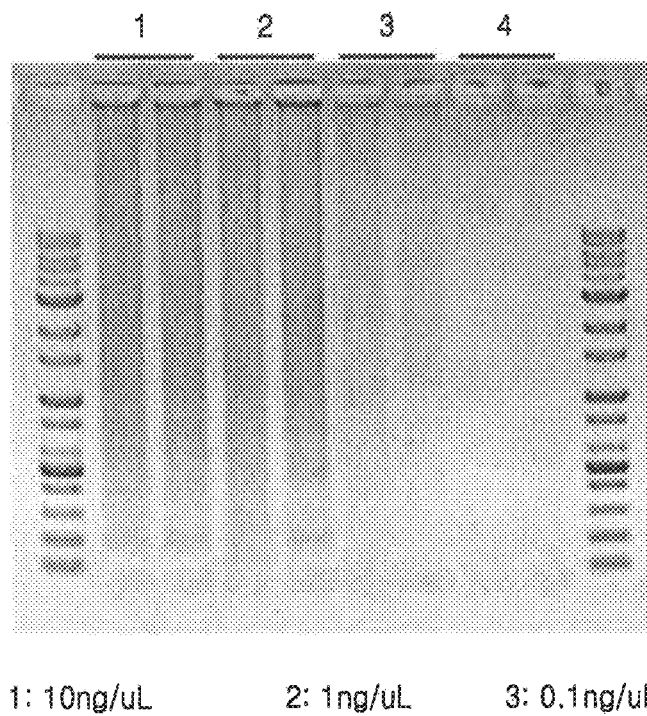
FIG. 3A shows a result for isothermal amplification products of nucleic acids, as identified by electrophoresis.
Figure 3B:
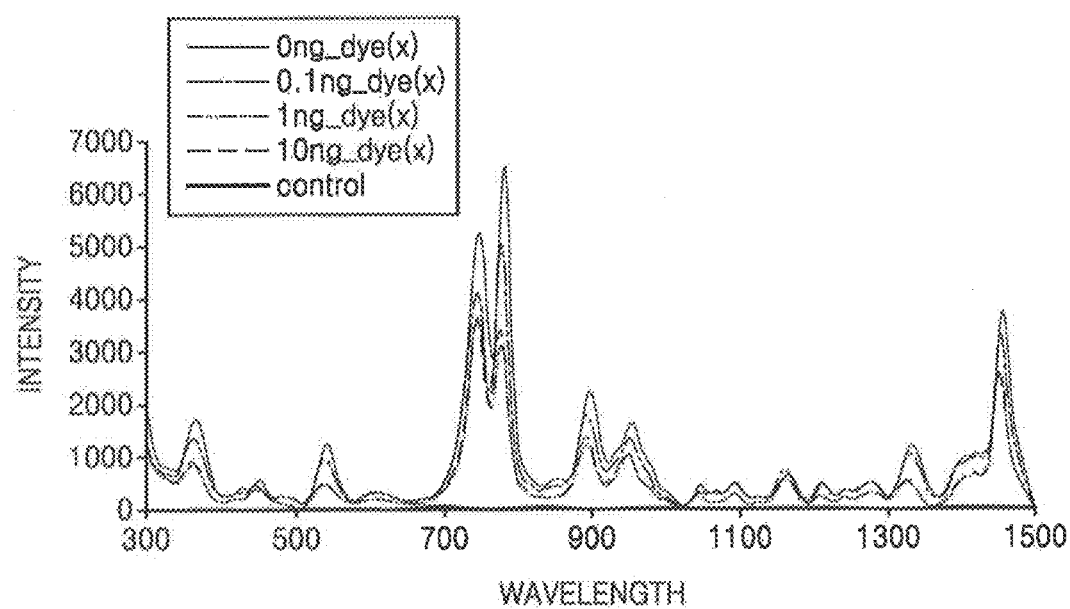
FIGS. 3B and 3C are graphs showing Raman spectrum measurement results for isothermal amplification products of nucleic acids, identified from the second porous substrate produced as in example 3 below.
Figure 3C:
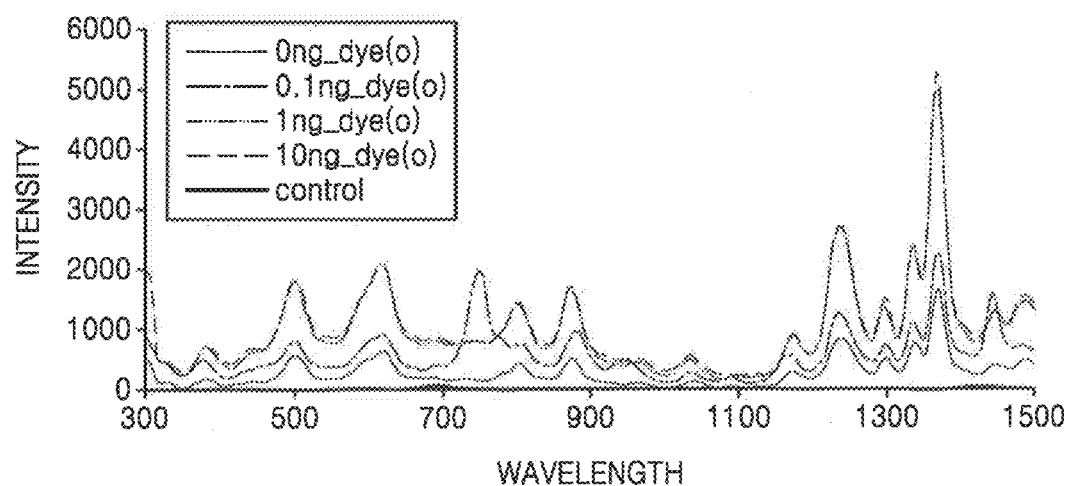

Each 10 µℓ of the reaction products was loaded on a 1% agarose gel and was then subjected to electrophoresis to identify the quantity of the reaction product. In addition, each 10 µℓ of the reaction product was dispensed to a 0.5 cm×0.5 cm substrate produced as in example 3 above, followed by performing Raman spectrum measurement. The Raman spectrum measurement was performed using a high-resolution dispersive Raman microscope (Horiba Jobin Yvon, LabRAM HR, 632.8 nm, HeNe laser). The laser power was 0.4 mW, and the accumulation time was set to 0.5 seconds. FIG. 3A shows a result for isothermal amplification products of nucleic acids, as identified by electrophoresis, and FIGS. 3B and 3C are graphs showing Raman spectrum measurement results for isothermal amplification products of nucleic acids, identified from the second porous substrate produced as in example 3 above. Here, FIG. 3B shows scattering signals of samples without SYBR green in the LAMP mix solution, and FIG. 3C shows scattering signals of samples with SYBR green in the LAMP mix solution. As confirmed from FIG. 3B, as the quantity of the target nucleic acid was increased, the Raman scattering signal of the nucleic acid was attenuated, and Raman scattering signal wavelengths of about 800 to 1000 nm, and about 1300 to 1500 nm were shifted by polymerization. However, as confirmed from FIG. 3C, in the presence of SYBR green, as the quantity of nucleic acids was increased, the Raman scattering signal of SYBR green had an increased intensity. Therefore, it is understood that the target nucleic acid can be rapidly and accurately detected by identifying Raman scattering from the isothermal amplification products of nucleic acids on the second porous substrate of the present invention.

5. Isothermal Amplification of Nucleic Acid on Porous Fiber Substrate Having Silver Nanowire and Detection of Target Gene Through Raman Scattering A nucleic acid was isothermally amplified on the second porous substrate produced as in example 3 above, and surface-enhanced Raman scattered light was detected, thereby identifying whether the target gene was present in the sample.

Loop-mediated isothermal amplification (LAMP) was selected as an isothermal gene amplification technique, and a LAMP kit (bioassay) fabricated for marine birnavirus was used. A LAMP mix solution including BST DNA polymerase, BSP polymerase buffer, dNTP mix, LAMP prime mix SYBR green, and marine birnavirus RNA, was prepared. 10 µℓ of the LAMP mix solution was dispensed to a 0.5 cm×0.5 cm substrate produced as in example 3 above, and 20 µℓ of the LAMP mix solution was put into a 300 µℓ tube for PCR. After the PCR reaction was conducted at 65° C. for one hour, the reaction was terminated.

Figure 4:
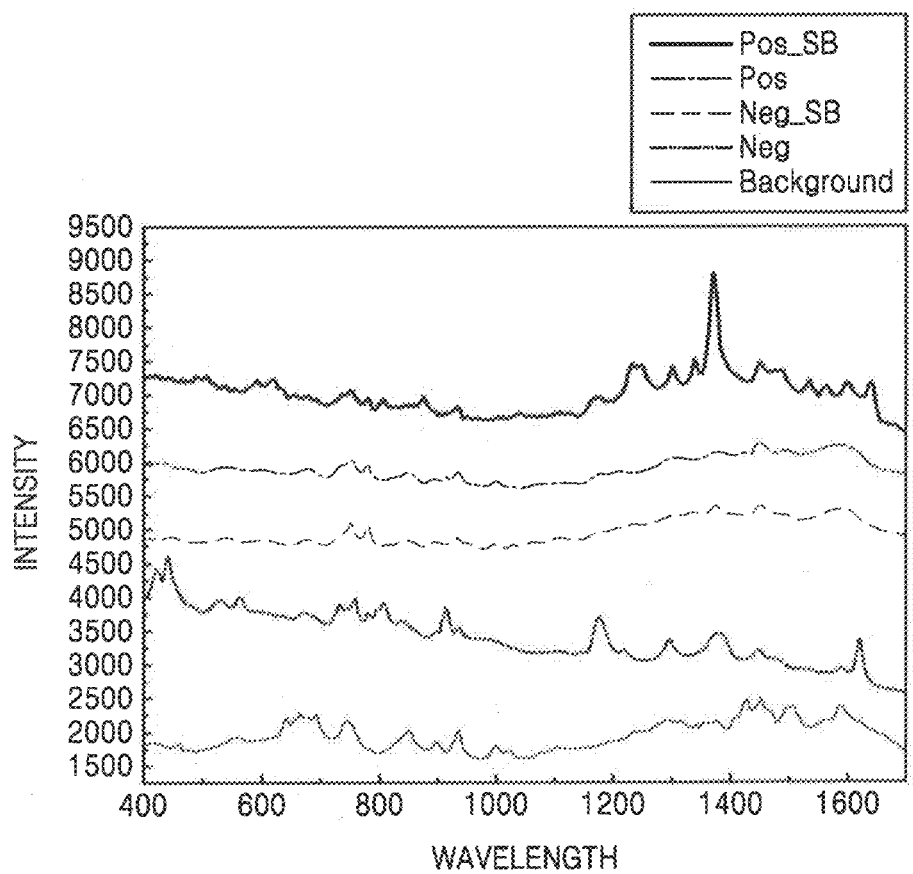
FIG. 4 is a graph illustrating a Raman spectrum measurement result, from which amplification of nucleic acids included in the porous substrate is identified.

The Raman spectrum was measured using a high-resolution dispersive Raman microscope (Horiba Jobin Yvon, LabRAM HR, 632.8 nm, HeNe laser). The laser power was 0.4 mW and the accumulation time was set to 0.5 seconds. FIG. 4 is a graph illustrating a Raman spectrum measurement result, from which amplification of nucleic acids included in the porous substrate is identified. Group 1 represents a scattering signal (Pos_SB) of a sample containing a LAMP mix solution. Group 2 represents a scattering signal (Background) of a sample acquired from the substrate produced as in example 3 above, group 3 represents a scattering signal (Neg) of a marine virnavirus RNA- and SYBR green-free sample in the LAMP mix solution, group 4 represents a scattering signal (Neg_SB) of a marine virnavirus RNA-free sample in the LAMP mix solution, and group 5 represents a scattering signal (Pos) of an SYBR green-free sample in the LAMP mix solution. As shown in FIG. 4, referring to group 1 (Pos_SB) and group 4 (Neg_SB), it was confirmed that group 1 (Pos_SB) with marine virnavirus RNA and SYBR green had a greatly enhanced Raman scattering signal in the wavelength range from about 1200 nm to about 1400 nm. In the cases of group 3 (Neg) and group 5 (Pos) without SYBR green, it was confirmed that an isothermal amplification phenomenon occurred to group 5 with marine virnavirus RNA, and that Raman scattering signals of nucleic acids were attenuated.

Therefore, it can be understood that the target nucleic acid is amplified by the isothermal amplification reaction conducted on the second porous substrate of the present invention, and the target nucleic acid can be rapidly and accurately detected by identifying Raman scattering on the same substrate.

6. Nucleic Acid Amplification Through PCR and Target Gene Detection Through Raman Scattering on Porous Fiber Substrate Having Silver Nanowire PCR was conducted to identify the efficacy of nucleic acid detection on the second porous substrate produced as in the example 3 above. Specifically, various concentrations including 10 ng, 100 pg, 10 pg, 1 pg, 0.1 pg, 0.02 pg and 0 of Influenzae A cDNA template as a target nucleic acid, were mixed in with 20 µℓ of a PCR master mixture (including SYBR green). Thereafter, the reaction was conducted at 50° C. for 2 minutes; at 95° C. for 2 minutes; at 95° C. for 15 seconds; and at 60° C. for one minute; and a total of 40 cycles were run. Then, each 10 µℓ of the PCR products were loaded on a 1% agarose gel and the quantities of the reaction products were identified by electrophoresis. In addition, each 10 µℓ of the reaction products was dispensed to a 0.5 cm×0.5 cm substrate produced as in the example 3 above and then subjected to Raman spectrum measurement.

Figure 5A:
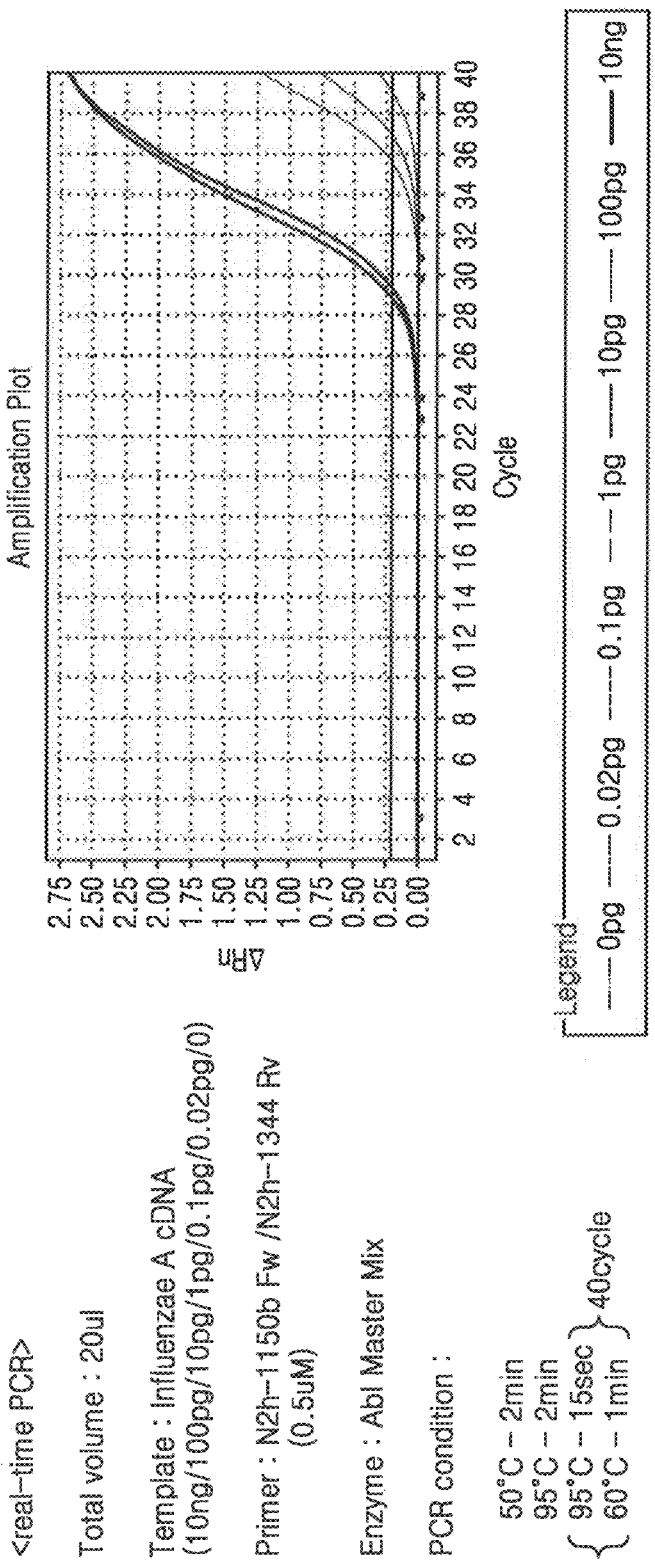
FIG. 5A shows a graph illustrating a real-time PCR result.
Figure 5B:
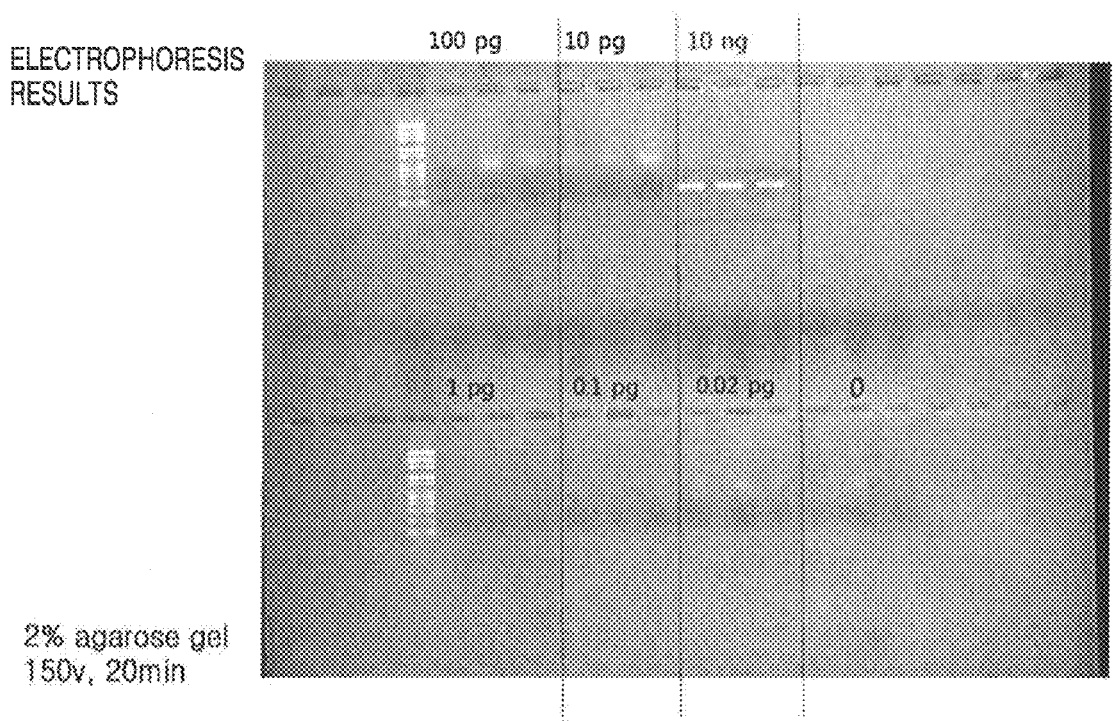
FIG. 5B shows an electrophoresis result for PCR products.

FIG. 5A shows a graph illustrating a real-time PCR result, and FIG. 5B shows an electrophoresis result for PCR products. As shown in FIG. 5A, it was confirmed that significant amplification was detected only at 10 ng and slight amplification occurred at 100 pg. In addition, as shown in FIG. 5B, the result of electrophoresis performed on the amplified products also confirmed that a distinct band was observed at 10 ng.

Figure 6:
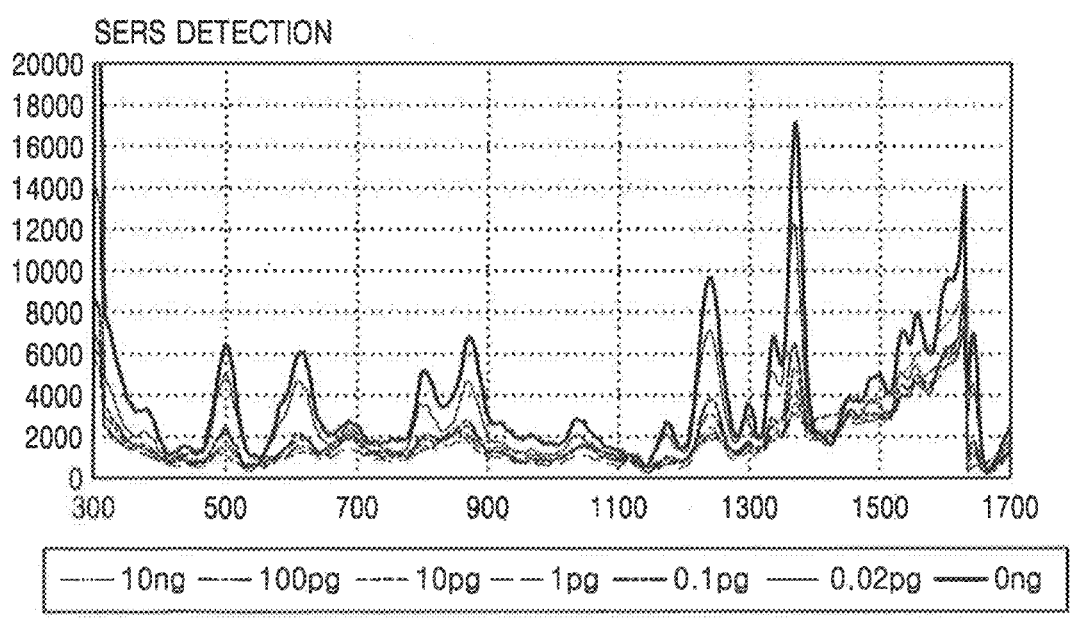
FIG. 6 shows a graph illustrating Raman spectrum measurement results analyzed after dropping PCR products on a porous substrate.

FIG. 6 shows a graph illustrating Raman spectrum measurement results analyzed after dropping PCR products on a second porous substrate. As shown in FIG. 6, it was confirmed that SERS signals varied with various concentrations of nucleic acids. That is to say, it could be confirmed that the SERS signals were generally attenuated as the quantity of amplified genes was increased. This could be attributable to the inability of SYBR green to interact with an SERS hot-spot if the SYBR green is chelated with amplified double stranded DNAs. Unlike in the electrophoresis detection of the PCR amplification products, in SERS detection, it could be confirmed that a statistically significant result was demonstrated even at 0.02 pg.

The above results tend to be contrary to those of SERS signals of isothermal amplification products, which is expected to appear due to a difference in the interaction mechanism between an SERS substrate and the hot-spot, because the PCR products have a constant molecular weight, whereas the isothermal amplification products have various molecular weight sizes ranging from lower molecular weight to higher molecular weight.

The invention claimed is:

1. A method for detecting a target gene comprising:
   contacting a biological sample with a first porous substrate supporting a composition for nucleic acid detection and thus extracting a nucleic acid from the biological sample;
   contacting the extracted nucleic acid with a second porous substrate having a metal nanostructure and thus bringing the nucleic acid into proximity to the metal nanostructure, wherein the bringing of nucleic acid into proximity to the metal nanostructure comprises an isothermal amplification reaction, and the isothermal amplification reaction is conducted at a temperature ranging from 37° C. to 80° C.; and
   acquiring a signal of the light scattered after irradiating with laser the second porous substrate having the nanostructure to which the nucleic acid is brought into proximity.

2. The method of claim 1, wherein the biological sample includes tissue, a cell, blood, blood plasma, blood serum, saliva, sputum, spinal fluid, urine, or a combination thereof.

3. The method of claim 1, wherein, when the first porous substrate and the second porous substrate are arranged to be in contact with each other, the extracted nucleic acid moves from the first porous substrate to the second porous substrate in direct contact with each other.

4. The method of claim 1, wherein the scattering is surface-enhanced Raman scattering (SERS), surface-enhanced resonance Raman scattering (SERRS), coherent anti-stokes Raman scattering (CARS), or a combination thereof.

5. The method of claim 1, wherein the scattering signal is a scattering signal intensity, a scattering signal pattern, or a combination thereof.

* * * * *